United States Patent
Schell et al.

(10) Patent No.: US 11,273,328 B2
(45) Date of Patent: Mar. 15, 2022

(54) IRRADIATION TREATMENT PLANNING BASED ON TARGET COVERAGE REDUCTION

(71) Applicant: Brainlab AG, Munich (DE)

(72) Inventors: Stefan Schell, Munich (DE); Claus Promberger, Pfaffenhofen (DE)

(73) Assignee: BRAINLAB AG, Munich (DE)

( * ) Notice: Subject to any disclaimer, the term of this patent is extended or adjusted under 35 U.S.C. 154(b) by 320 days.

(21) Appl. No.: 16/328,653

(22) PCT Filed: Mar. 2, 2018

(86) PCT No.: PCT/EP2018/055207
§ 371 (c)(1),
(2) Date: Feb. 26, 2019

(87) PCT Pub. No.: WO2019/166105
PCT Pub. Date: Sep. 6, 2019

(65) Prior Publication Data
US 2020/0069972 A1    Mar. 5, 2020

(51) Int. Cl.
*A61N 5/10* (2006.01)

(52) U.S. Cl.
CPC ......... *A61N 5/1069* (2013.01); *A61N 5/1031* (2013.01)

(58) Field of Classification Search
CPC ............................ A61N 5/1069; A61N 5/1031
See application file for complete search history.

(56) References Cited

U.S. PATENT DOCUMENTS

2011/0306818 A1   12/2011   Bert et al.
2017/0259083 A1*   9/2017   Nakatsugawa ...... A61N 5/1049

FOREIGN PATENT DOCUMENTS

WO   WO2018070109 A1   4/2018

OTHER PUBLICATIONS

Brainlab AG Germany, Cranial SRS Software User Guide, Revision 1.0, Version 1.0, 2017, Retrieved on Feb. 8, 2017, 104 Pages.
International Search Report and Written Opinion issued in PCT Application No. PCT/EP2018/055207 dated Nov. 20, 2018.

* cited by examiner

*Primary Examiner* — Christine H Matthews
*Assistant Examiner* — Joshua Daryl D Lannu
(74) *Attorney, Agent, or Firm* — Middleton Reutlinger

(57) ABSTRACT

A computer-implemented medical method of irradiation treatment planning is provided. Therein, an initial coverage volume for a planning target volume, which is to be irradiated in an irradiation treatment with a prescribed dose, is provided. Further, at least one constraint indicative of an allowed dose for an organ at risk is provided. Applying an initial irradiation treatment plan, an organ dose deposited in at least a partial volume of the organ at risk is calculated. Based on comparing the organ dose to the at least one constraint, an amount of violation is determined. Taking into account the determined amount of violation, a reduction coverage volume is calculated for the planning target volume and a virtual planning object is generated based on changing a volume of the organ at risk, such that an overlap region of the virtual planning object and the planning target volume corresponds to the reduction coverage volume. By removing at least a part of the overlap region from the planning target volume, an optimized planning target volume is generated.

15 Claims, 5 Drawing Sheets

IRRADIATION TREATMENT PLANNING BASED ON TARGET COVERAGE REDUCTION

FIELD OF THE INVENTION

The present invention relates to a computer-implemented medical method for irradiation treatment planning, a corresponding computer program, a non-transitory program storage medium storing such a program and a computer for executing the program, as well as a medical system comprising an electronic data storage device and the aforementioned computer.

TECHNICAL BACKGROUND

For irradiation treatment planning in the field of radiotherapy and/or radiosurgery, a planning target volume associated with or representing e.g. a tumor, a metastasis and/or cancerous tissue, is specified along with a desired prescribed dose. The prescribed dose should preferably be deposited in at least a partial volume, also referred to as coverage volume, of the planning target volume in order to ensure biological effectiveness of the irradiation treatment. Apart from that, one or more constraints to be fulfilled during irradiation treatment can be specified. Typically, an organ at risk, which preferably is to be spared during irradiation treatment or which should not receive more than an allowed dose in at least a partial volume thereof, can be specified as constraint. Based on the specified planning target volume, the prescribed dose and the one or more constraints, usually the coverage volume of the planning target volume is determined and a corresponding irradiation treatment plan is generated. The irradiation treatment plan can then be utilized to carry out the actual irradiation treatment.

In certain scenarios, however, a prescribed dose may not be deposited in a desired coverage volume of the planning target volume without affecting the organ at risk, and thereby potentially violating one or more of the specified constraints. This can, for instance, be the case if the planning target volume is located in vicinity of the organ at risk.

Accordingly, a trade-off and compromise between the coverage volume of the planning target volume, in which a biologically effective dose is to be deposited, and a dose deposition or a sparing of the organ at risk should be found in order to, preferably, fulfil one or more constraints for the organ at risk.

In current irradiation treatment planning, it is a common procedure to manually reduce the coverage volume of the planning target volume in order to ensure fulfilment of the one or more constraints. Such manual adjustment or reduction of the coverage volume, however, can be time consuming and/or error-prone. For example, a coverage volume, which is too large, can lead to the violation of at least one constraint, whereas a coverage volume, which is too small, can lead to an unnecessarily low dose deposition in the planning target volume, thereby reducing the effectiveness of the irradiation treatment.

It is, therefore, desirable to provide for an improved method of irradiation treatment planning, e.g. allowing to automatically and precisely determine an optimum trade-off between the coverage volume and at least one constraint to be fulfilled with respect to an organ at risk.

The present invention can be used for radiotherapy or radiosurgery procedures, such as the cranial/spine stereotactic radiosurgery treatment planning system, e.g. in connection with a system for image-guided radiotherapy such as VERO® and ExacTrac®, all products of Brainlab AG.

Aspects of the present invention, embodiments, examples and exemplary steps are disclosed in the following. Different embodiments, examples and exemplary features of the invention can be combined in accordance with the invention wherever technically expedient and feasible.

Moreover, it is emphasized that any feature, element and/or step described in the following with respect to one aspect of the invention equally applies to any other aspect of the invention.

Emplary Short Description of the Invention

In the following, a short description of the specific features of the present invention is given which shall not be understood to limit the invention only to the features or a combination of the features described in this section.

The disclosed method comprises providing an initial coverage volume for a planning target volume, which is to be irradiated in an irradiation treatment with a prescribed dose. The planning target volume can be associated with e.g. one or more tumors, one or more metastases, cancerous tissue and/or any other tissue of a patient. Further, at least one constraint for an organ at risk is provided. Generally, the organ at risk can refer to any vital organ, such as e.g. a brainstem, an eye, an eye nerve, and/or any other tissue or part that might be relevant for a vital function of the patient and/or that preferably should be preserved. According to the at least one constraint, an allowed dose deposited in at least a partial volume of the organ at risk can be specified.

Applying an initial or current irradiation treatment plan, an organ dose deposited in at least a partial volume of the organ at risk is calculated. The calculated organ dose is then compared to the at least one constraint and an extent or amount of violation of this constraint is determined. The amount of violation may be indicative of an excessive dose deposited in at least the partial volume of the organ at risk, e.g. exceeding the allowed dose as indicated by the constraint.

Taking into account the determined amount of violation, a reduction coverage volume is calculated for the planning target volume and a virtual planning object is generated based on changing, modifying, varying and/or adjusting a volume of the organ at risk. Therein, the volume of the virtual planning object, which corresponds to the changed volume of the organ at risk, is determined, such that an overlap region of the virtual planning object and the planning target volume substantially matches and/or substantially equals the reduction coverage volume, as determined based on the amount of violation. Generally, the virtual planning object may be generated based on increasing (e.g. expanding) or decreasing (e.g. shrinking and/or reducing) the volume of the organ at risk.

The initial coverage volume of the planning target volume is then reduced based on removing at least a part of the overlap region of the virtual planning object and the planning target volume. Thereby, an optimized planning target volume, which may refer to an optimized coverage volume of the planning target volume, is generated.

Taking into account the optimized planning target volume and/or disregarding the volume removed from the initial planning target planning, an updated or optimized irradiation treatment plan can be determined and/or generated. The updated or optimized irradiation treatment plan can be used later on in a medical system, e.g. comprising a radiation treatment apparatus, to control and/or instruct the medical system to perform the actual irradiation treatment on a patient thereby using the optimized planning target volume.

It is noted that the optimized planning target volume can be iteratively determined in an iteration process, preferably a fully automated and/or automatic iteration process, particularly in order to find the optimum trade-off between the coverage volume and the at least one constraint to be fulfilled with respect to an organ at risk, as will be discussed in more detail in the following.

In the context of the present disclosure, a "volume", "object" and/or the "the organ at risk" may generally refer to a geometrical object, a geometrical shape and/or a geometrical structure. The volume, object and/or organ at risk may comprise e.g. a shape, a contour, an orientation, a position, a spatial position, a content and/or a spatial content. This may particularly apply to the terms "planning target volume", "organ at risk", "virtual planning object", "optimized planning target volume", and/or "auxiliary planning object". Moreover, any volume, object and/or the organ at risk referred to in the present disclosure may be represented in and/or provided by a voxel representation, such as e.g. a voxel representation of at least a part of a patient. Accordingly, any "volume", "object" and/or the "organ at risk" in the context of the present disclosure may also refer to and/or comprise a subset of voxels in the voxel representation.

Moreover, the term "coverage volume" as used in the context of the present disclosure, such as e.g. the terms "initial coverage volume", "reduction coverage volume", "tolerated coverage volume", and "desired coverage volume" each may refer to a volume value, such as an absolute volume value or a relative value (e.g. with respect to a reference volume). By way of example, the initial coverage volume may be given as a relative volume value, e.g. a certain percentage, of the planning target volume. The same may apply to any other "coverage volume" referred to in the context of the present disclosure.

It is emphasized, however, that the present disclosure is not limited in this respect. Rather, also any "coverage volume" may refer to a geometrical object, a geometrical shape and/or a geometrical structure. Accordingly, also any "coverage volume" may comprise e.g. a shape, a contour, an orientation, a position, a spatial position, a content, a spatial content, and/or a subset of voxels in the voxel representation, as described above with reference to the terms "volume", "object" and/or "organ at risk".

General Description of the Invention

In the following section, a description of the general features of the present invention is given, for example by referring to possible embodiments of the invention.

As stated above, it may be desirable to provide for an improved method of irradiation treatment planning, which for example allows to determine an optimum trade-off and/or compromise between the coverage volume of a given planning target volume and at least one constraint for an organ at risk.

This is achieved by the subject-matter of the independent claims, wherein further embodiments are incorporated in the dependent claims and the following description.

According to a first aspect of the invention, a computer-implemented medical method of irradiation treatment planning is provided. The method comprises the following steps:

providing an initial coverage volume for a planning target volume to be irradiated in an irradiation treatment with a prescribed dose;

providing at least one constraint for an organ at risk, the at least one constraint being indicative of an allowed dose deposited in and/or delivered to at least a part or a partial volume of the organ at risk;

calculating an organ dose deposited in and/or delivered to said at least part or partial volume of the organ at risk when applying an initial irradiation treatment plan;

determining an amount of violation of the at least one constraint based on comparing the at least one constraint and the calculated organ dose;

calculating a reduction coverage volume for the planning target volume based on the determined amount of violation;

generating a virtual planning object by changing, modifying, adapting, varying, and/or adjusting a volume of the organ at risk, such that an overlap region of the virtual planning object with the planning target volume corresponds to the reduction coverage volume; and reducing the initial coverage volume of the planning target volume based on removing at least a part of said overlap region from the planning target volume, thereby generating an optimized planning target volume to be irradiated during the irradiation treatment.

Calculating the reduction coverage volume based on the determined amount of violation of the at least one constraint and reducing the initial coverage volume of the planning target volume taking into account the calculated reduction coverage volume, advantageously allows to find and/or determine an improved and/or controlled compromise between irradiating the planning target volume and sparing the organ at risk during the actual irradiation treatment. Here and in the following, the sparing of the organ at risk may refer to minimizing the organ dose deposited in the organ at risk or a partial volume thereof and/or avoiding any dose deposition in the organ at risk. Accordingly, a deterministic procedure for finding this compromise may be provided by the present invention. Apart from that, the procedure and/or the determination of the compromise, and hence the previously determined optimized planning target volume, may be fully automated or may be carried out in a fully automated manner.

It is noted that the present invention can be employed for planning an actual irradiation treatment using any type of ionizing radiation, such as e.g. photons, protons, electrons, positrons, alpha particles, ions, neutrons or any other radiation, particularly ionizing radiation.

Generally, the planning target volume can be indicative of, associated with and/or represent a target volume of a patient to be at least partly irradiated during the irradiation treatment. Such target volume may, for instance, be one or more tumors, one or more metastases, cancerous tissue and/or any other tissue of the patient to be treated with a radiation beam of ionizing radiation in the radiation treatment. Accordingly, the planning target volume may refer to a representation of the patient's target volume to be irradiated in the irradiation treatment.

The initial coverage volume of the planning target volume may refer to, be indicative of and/or represents a partial volume or the entire planning target volume, in which e.g. the prescribed dose is to be deposited in the irradiation treatment. Therein, the initial coverage volume may be given in and/or defined as an absolute value or as a relative value. In the latter case, the initial coverage volume may be normalized to any volume, such as e.g. the planning target volume.

Further, the organ at risk can refer to, be indicative of and/or represent any vital organ, such as e.g. a brainstem, an eye, an eye nerve, and/or to any other tissue that might be relevant for a vital function of the patient. Accordingly, the organ at risk referred to above and in the following may be a representation of any part, organ or tissue of the patient, which preferably should be spared or preserved during the actual irradiation treatment.

The at least one constraint of the organ at risk may be indicative of, represent and/or correlate with a maximum allowed dose delivered to and/or deposited in at least a partial volume of the organ at risk. The maximum allowed dose can, for instance, refer to a maximum dose value that should not be deposited in any part of the organ at risk.

Alternatively or additionally, the at least one constraint may be indicative of, represent and/or correlate with a maximum cumulative dose delivered to and/or deposited in at least a part of the organ at risk. For instance, the maximum cumulative dose can be given as a certain dose value (or allowed dose) deposited in a certain partial volume of the organ at risk, which dose value should not be exceeded. Accordingly, the allowed dose indicated by the at least one constraint may refer to any or both the maximum allowed dose and the maximum cumulative dose. However, also any other dose may be indicated by the at least one constraint as allowed dose.

The amount of violation of the at least one constraint may be indicative of, represent and/or correlate with a deviation of the calculated organ dose and the at least one constraint. By way of example, the amount of violation may be given as an excessive dose exceeding the allowed dose, as indicated by the at least one constraint. Such amount of violation may be given in absolute or relative value, e.g. normalized to the allowed dose. The amount of violation may e.g. be determined based on subtracting the calculated organ dose and the allowed dose. Alternatively or additionally, the amount of violation may be determined based on determining a ratio of the calculated organ dose and the allowed dose.

The reduction coverage volume may refer to and/or be indicative of a partial volume of the planning target volume. According to the determined amount of violation, the reduction coverage volume can be determined as the partial volume of the planning target volume, which is to be removed from the planning target volume in order to reduce the amount of violation and/or to preferably fulfil the at least one constraint. Accordingly, the reduction coverage volume can be regarded as a "sacrificed" partial volume of the planning target volume, which is to be removed from the planning target volume. The reduction coverage volume can e.g. be determined, such that the amount of violation is reduced and/or such that the at least one constraint is fulfilled. Generally, the reduction coverage volume can be given in absolute or relative value. For example, the reduction coverage volume can be normalized to the planning target volume or the initial coverage volume.

Moreover, the optimized coverage volume may refer to and/or be indicative of a partial volume of the planning target volume and/or of the initial coverage volume. Particularly, the optimized coverage volume may refer to and/or be indicative of the planning target volume reduced by at least a part of the reduction coverage volume. Alternatively or additionally, the optimized coverage volume may refer to and/or be indicative of the initial coverage volume reduced by at least a part of the reduction coverage volume. For example, the optimized coverage volume can be determined and/or generated, such that the determined amount of violation is reduced and/or such that the at least one constraint for the organ at risk is fulfilled, e.g. when irradiating only the optimized coverage volume.

The term "virtual planning object" may refer to an abstract object or structure resulting from changing the size and/or volume of the organ at risk. Therein, the size and/or volume of the organ at risk may be changed based on increasing or decreasing the size and/or volume of the organ at risk, thereby generating the virtual planning object. Such changing of the volume of the organ at risk may be performed virtually and/or without being visible to a user, e.g. a user applying the method according to the invention and/or using a corresponding program, software, computer and/or medical system. For example, the virtual planning object may be generated based on expanding (and/or increasing) or shrinking (reducing and/or decreasing) the organ at risk, a contour of the organ at risk, a circumference of the organ at risk and/or a perimeter of the organ at risk. Alternatively or additionally, the virtual planning object may be generated based on increasing or decreasing a diameter and/or cross-section of the organ at risk, e.g. in one or more planes intersecting the organ at risk.

In order to generate the virtual planning object, the volume and/or size of the organ at risk may be changed, by way of example, by about 0.5% to about 25%, preferably about 0.5% to about 15%, more preferably by about 1% to about 10%, and even more preferably by about 2% to about 5%. Therein, the percentage values may be measured relative to the volume and/or an actual volume of the organ at risk.

Further, the overlap region may refer to an overlap volume and/or a partial volume of the planning target volume, which intersects and/or overlaps with the virtual planning object and/or a partial volume thereof. Accordingly, the overlap region may be determined based on determining intersecting volumes of the planning target volume and the virtual planning object. In other words, the overlap region may refer to a region or volume of the planning target volume which is covered by at least a partial volume of the virtual planning object.

Generally, generating the virtual planning object and/or determining the overlap region may advantageously allow to determine the part or partial volume of the planning target volume, which may be located nearer to the organ at risk than remaining parts of the planning target volume. Reducing the planning target volume by this partial volume or a part thereof may have a larger effect on reducing the amount of violation with respect to removing other parts of the planning target volume. Accordingly, based on the virtual planning object, a position information may be determined and/or derived in terms of where and/or which partial volume of the planning target volume should be removed based on the calculated reduction coverage volume. Particularly, this may allow to effectively reduce, minimize and/or eliminate the amount of violation.

Rephrasing the first aspect of the present invention, the initial coverage volume may be received, e.g. via a user input, and/or retrieved from a data storage device. Further, the at least one constraint for the organ at risk may be received, e.g. via a user input, and/or retrieved from the data storage device. Based on and/or applying the initial irradiation treatment plan, the organ dose deposited in at least a part of the organ at risk is calculated, determined and/or estimated. Such calculation may, for instance, be based on a simulation, a simulation calculation, a Monte Carlo simulation, an approximation and/or a modelling of the actual irradiation treatment. For such purposes an optimisation function can be used as will be described hereinafter with more detail. The calculated dose can then be compared to the allowed dose as indicated by the at least one constraint in order to determine the amount of violation. Accordingly, the amount of violation may serve as an indicator for an extent of the violation of the at least one constraint, e.g. according to the initial irradiation treatment plan. The determined amount of violation may then be converted to the reduction coverage volume. Further, the organ at risk may be changed in size and/or volume, e.g. expanded or shrunk, to generate the virtual planning object, such that a partial volume thereof overlaps with the planning target volume in the overlap region. Therein, the volume and/or change in volume of the virtual planning object may be chosen, such that the overlap region substantially matches and/or substantially equals the determined reduction coverage volume. To finally determine and/or generate the optimized planning target volume, at least a part of the overlap region is removed from planning target volume, e.g. thereby reducing, minimizing and/or eliminating the amount of violation. This allows a precise and fast determination of a good compromise between coverage volume of the planning target volume and the sparing of the organ at risk. This can easily be retraced from e.g. the embodiment described in the context of FIGS. 3A to 3E.

Generally, the invention may be considered as being based on the following insights and findings. In preparation of the actual irradiation treatment, i.e. before performing or carrying out the irradiation treatment, a dose deposited in the planning target volume, any surrounding tissue and/or the organ at risk can be determined using an initial irradiation treatment plan, e.g. based on a simulation or simulation calculation. This allows to determine whether the organ at risk or any partial volume thereof would be affected, if the planning target volume was irradiated according to the initial irradiation treatment plan. Such affection of the organ at risk, can occur for example if the organ at risk is located close to, near, adjacent and/or in vicinity of the planning target volume. Also, the organ at risk can at least partially overlap with the planning target volume. However, the organ at risk can also be affected by an irradiation of the planning target volume, if for example an improper beam direction and/or an improper energy distribution of the radiation beam is chosen. For instance, depending on the type of ionizing radiation used, a penetration depth of the ionizing particles and/or scattering effects can result in dose deposition far away from the planning target volume, thereby potentially affecting the organ at risk by depositing energy within the organ at risk. In conventional approaches and/or procedures for irradiation treatment planning in the prior art, the planning target volume (and/or the initial coverage volume) is manually reduced in order to ensure the sparing of the organ at risk, i.e. to keep the dose deposited in the organ at risk as low as possible. However, the size and/or amount of the reduced planning target volume and/or the reduction coverage volume is not obvious. Accordingly, it may be challenging to determine the reduction coverage volume with high accuracy and precision in such manual approach. Particularly, the amount of reduction and/or the reduction coverage volume is not obvious before optimizing an irradiation treatment plan, e.g. in terms of settings of a medical system and/or a radiation treatment apparatus. Accordingly, reducing the planning target volume can be time consuming and/or error prone. Also, the procedure of finding an optimum reduced planning target volume and/or the optimized planning target volume may require an iterative, and hence manual, reduction of the planning target volume multiple times. This, in turn, may require a restart of the entire optimization of the irradiation treatment plan in each iteration step of the prior art.

All such drawbacks mentioned hereinbefore are overcome by the present invention, as the reduction coverage volume and/or the optimized planning target volume may advantageously be determined based on the amount of violation for the one or more constraints. This may allow for a more controlled, predictable and/or precise determination of the optimized planning target volume. Also, the optimized planning target volume may be determined much faster, effectively and/or efficiently. Overall, the invention allows to find and/or determine an appropriate and/or optimum trade-off between irradiating the planning target volume and sparing of the organ at risk during the process of irradiation treatment planning.

It is emphasized, that the invention solely relates to irradiation treatment planning. Accordingly, the invention does not involve or in particular comprise or encompass an invasive step which would represent a substantial physical interference with the body of a patient requiring professional medical expertise to be carried out and entailing a substantial health risk even when carried out with the required professional care and expertise. Particularly, the invention does not involve, comprise and/or encompass any surgical or therapeutic activity. The invention is instead directed as applicable to irradiation treatment planning before carrying out the actual irradiation treatment on the patient. For this reason alone, no surgical or therapeutic activity and in particular no surgical or therapeutic step is necessitated or implied by carrying out the invention.

According to an embodiment of the invention, the method further comprises the step of converting and/or translating the calculated reduction coverage volume into a radius for the virtual planning object, wherein the virtual planning object is generated based on changing, e.g. increasing or decreasing, the volume of the organ at risk using said radius.

Therein, the radius may refer to a value of a margin, such as e.g. an increment parameter (or increment value) or a decrement parameter (or decrement value), by which at least a part of the organ at risk is changed, e.g. increased and/or expanded or decreased, reduced and/or shrunk, respectively. For example, at least a part of a contour, outer surface, perimeter and/or circumference of the organ at risk may be changed (e.g. increased or decreased) based on the radius, thereby generating the virtual planning object. Accordingly, the radius may refer to and/or correlate with a distance between at least a part of the outer surface, contour, perimeter and/or circumference of the organ at risk and at least a part of an outer surface, contour, perimeter and/or circumference of the virtual planning object. Generally, converting the calculated reduction coverage volume into the radius for the virtual planning object advantageously allows to efficiently, quickly and precisely determine the optimized planning target volume, particularly in a controlled and/or automated manner.

According to an embodiment, changing the volume of the organ at risk comprises increasing or decreasing the volume of the organ at risk. In other words, the virtual planning object may be generated based on increasing (e.g. expanding) the volume of the organ at risk or based on decreasing (e.g. reducing and/or shrinking) the volume of the organ at risk. The latter may be particularly advantageous in a scenario, in which the organ at risk overlaps and/or intersects with the planning target volume.

According to an embodiment of the invention, the method further comprises the steps of:

providing a list comprising a plurality of pairs of entries, each pair of entries specifying a radius of an auxiliary virtual planning object and an amount of overlap of the corresponding auxiliary planning object with the planning target volume; and converting the calculated reduction coverage volume into a radius for the virtual planning object based on at least one of the pairs of entries of the list.

Therein, the term "auxiliary planning objects" may be understood as "auxiliary virtual planning objects" and may refer to the organ at risk expanded or shrunk at least partially by a certain radius, margin, value of an increment parameter, value of a decrement parameter, volume decrement, and/or volume increment, thereby generating a certain overlap region and/or amount of overlap with the planning target volume. The amount of overlap, however, may also be zero for one or more of the auxiliary planning objects. In contrast to the virtual planning object, the auxiliary planning objects may serve to convert the calculated reduction coverage volume into the radius and/or to determine the radius for the virtual planning object, such that the overlap region thereof with the planning target volume substantially corresponds to the calculated reduction coverage volume. The amount of overlap of each of the auxiliary planning objects can be given in absolute or relative value, e.g. normalized to the planning target volume, the initial coverage volume and/or the organ at risk.

Accordingly, an auxiliary planning object may be generated based on changing, adapting, modifying, and/or varying the volume of the organ at risk, e.g. similar to the generation of the virtual planning object. Accordingly, an auxiliary planning object may be generated based on changing, adapting, modifying, and/or varying the volume of the organ at risk. In order to generate one or more auxiliary planning objects, the volume and/or size of the organ at risk may be changed, by way of example, by about 0.5% to about 50%, preferably about 0.5% to about 25%, more preferably by about 1 to about 10%, and even more preferably by about 2% to about 5%. Therein, the percentage values may be measured relative to the volume and/or an actual volume of the organ at risk.

Generally, the list can refer to a look-up table, which may e.g. be stored on a data storage device. The list can have a resolution of at least 0.05 mm, preferably at least 0.1 mm. In other words, the radii of consecutive pairs of entries may differ from one another by at least 0.05 mm, preferably by at least 0.1 mm. Providing the list with the pairs of entries and converting the calculated reduction coverage volume into the radius based on the list can speed-up the entire automatic process of generating the virtual planning object and/or of determining the optimized planning target volume, particularly since the list can be determined before actually optimizing the irradiation treatment plan, e.g. in terms of determining a set of settings of the medical system and/or the radiation treatment apparatus. As the generation of the auxiliary planning objects, and hence a determination of the pairs of entries of the list, may be computationally extensive, i.e. may require a rather large computing power and/or computing time, generating the list before carrying out the actual irradiation treatment planning may save time. In other words, the list may allow a quick lookup of the radius for a given reduction coverage volume and therefore can significantly speed-up the optimization of the irradiation treatment plan. However, it is emphasized that the list and/or the one or more auxiliary planning objects can also be generated during the process of determining and/or generating the optimized planning target volume and/or during optimizing the irradiation treatment plan.

By way of example, the radius for the virtual planning object may be derived and/or retrieved directly from the list. For instance, an amount of overlap, which substantially matches and/or is closest to the determined reduction coverage volume (among all pairs of entries), may be automatically searched and/or identified among the pairs of entries of the list. The radius for the virtual planning object may then be chosen and/or selected from this identified pair of entries. Alternatively or additionally, the virtual planning object may be generated based on an interpolation, e.g. a linear interpolation, of two or more pairs of entries of the list. For instance, the amounts of overlap of two or more pairs of entries can be interpolated in order to determine the amount of overlap corresponding to, matching and/or equalling the reduction coverage volume, and the corresponding radius for the virtual planning object can then be calculated based thereon. It is noted, however, that also a functional relationship between the amount of violation and the radius can be derived from the pairs of entries, e.g. based on a fitting and/or approximation. Such functional relationship may be used to determine and/or calculate the radius of the virtual planning object, e.g. for a given overlap region and/or reduction coverage volume.

According to an embodiment of the invention, the step of generating the virtual planning object comprises:

generating a plurality of auxiliary planning objects based on changing, e.g. increasing or decreasing, the volume of the organ at risk by a different radius for each of the plurality of auxiliary planning objects, e.g. such that each of the plurality of auxiliary planning objects has a different size and/or volume; and determining an amount of overlap of each of the plurality of auxiliary planning objects with the planning target volume.

Further, one of the plurality of auxiliary planning objects having an amount of overlap, which corresponds to the calculated reduction coverage volume, may be selected, preferably automatically, as the virtual planning object for carrying out at least one iteration of the method of the present invention. The selected virtual planning object may then be used to reduce the volume of the planning target volume based on removing at least a part of the corresponding overlap region therefrom.

According to an embodiment of the invention, the method further comprises the step of compiling a list comprising a plurality of pairs of entries, wherein each of the plurality of pairs of entries is indicative of one of the plurality of auxiliary planning objects. Alternatively or additionally, each of the plurality of pairs of entries is indicative of the radius of one of the plurality of auxiliary planning objects and the corresponding amount of overlap of said one of the plurality of auxiliary planning objects with the planning target volume. The list may then be used for the generation of the virtual planning object and/or for the determination of the radius of the virtual planning object during the determination of the optimized planning target volume and/or during optimizing the irradiation treatment plan.

According to an embodiment of the invention, the method further comprises the step of receiving a tolerated coverage volume for the planning target volume, wherein the tolerated coverage volume is indicative of a minimum volume of the planning target volume receiving a prescribed dose during the irradiation treatment, wherein the reduction coverage volume for the planning target volume is determined based on the amount of violation of the at least one constraint and based on the tolerated coverage volume.

Generally, the tolerated coverage volume may refer to a minimum volume or volume fraction of the planning target volume, in which the prescribed dose is to be deposited, particularly in order to ensure biological effectiveness of the irradiation treatment. Accordingly, the tolerated coverage volume may refer to a lower limit of the coverage volume and/or to a lower limit of a partial volume of the planning target volume, which should be irradiated during the irradiation treatment. Hence, the optimized planning target volume may refer to and/or have a coverage volume of the planning target volume between the initial coverage volume and the tolerated coverage volume. The tolerated coverage volume may be given in absolute value or in relative value, e.g. normalized to the planning target volume. Further, the tolerated coverage volume may be provided and/or received via a user input. Alternatively or additionally, the tolerated coverage volume may be retrieved and/or read from a file, e.g. a clinical protocol file, in which for example the tolerated coverage volume and the prescribed dose may be defined or specified by a medical doctor. Such clinical protocol file can for instance be specified by the user. Further, the tolerated coverage volume may e.g. be given in the form of and/or it may be determined based on a dose volume histogram.

Moreover, a desired coverage volume may optionally be received and/or provided, wherein the desired coverage volume may be indicative of a volume (or volume fraction) of the planning target volume which should preferably be irradiated with the prescribed dose or a further prescribed dose. Accordingly, the desired coverage volume may refer to an upper limit of the coverage volume and/or to an upper limit of a partial volume of the planning target volume, which should preferably be irradiated during the irradiation treatment and/or, in which the prescribed dose should preferably be deposited. Hence, the optimized planning target volume may have a coverage or coverage volume of the planning target volume between the desired coverage volume and the tolerated coverage volume. The desired coverage volume may be given in absolute value or in relative value, e.g. normalized to the planning target volume. Further, the desired coverage volume may be provided via a user input and/or it may be read from a file, e.g. the clinical protocol file. Further, the desired coverage volume may e.g. be given in the form of and/or it may be determined based on a dose volume histogram.

According to an embodiment of the invention, the at least one constraint is retrieved and/or read from a file, e.g. the clinical protocol file.

For example, the at least one constraint may be specified by a medical doctor and/or may be specified in the clinical protocol file. The clinical protocol file may, for instance, be stored on a data storage device. The clinical protocol file can e.g. be selected by a user via a user input. Alternatively or additionally, the at least one constraint is retrieved and/or received from a user input. Further, the at least one constraint may be given in the form of and/or it may be determined based on a dose volume histogram.

According to an embodiment of the invention, the method further comprises the step of calculating a dose distribution for at least a part of the planning target volume and at least a part of the organ at risk based on an optimization function, wherein at least a part of the overlap region of the virtual planning object with the planning target volume is disregarded in the calculation of the dose distribution.

The determination and/or calculation of the dose distribution may comprise minimizing/maximizing the optimization function. Therein, the optimization function may describe a deviation of a specified dose and a calculated or simulated dose deposited in at least a part of the planning target volume and/or the organ at risk when using a current set of settings for the medical system and/or the radiation treatment apparatus, e.g. according to the initial treatment plan. Regarding the planning target volume, the specified dose may refer to the prescribed dose for the planning target volume deposited in a partial volume thereof. Regarding the organ at risk, the specified dose may refer to the allowed dose deposited in at least a partial volume thereof, as indicated by the at least one constraint. The set of settings for the medical system and/or the radiation treatment apparatus taken into account for minimizing/maximizing the optimization function may, among others, comprise and/or relate to a particle energy and/or energy distribution of the radiation beam, a fluence rate of the beam, a flux of the beam, an intensity of the beam, one or more settings for a collimator and/or collimator leaves, a collimator shape, and/or any other parameter value related to the actual irradiation treatment. Generally, by calculating the dose distribution based on the optimization function and/or by minimizing/maximizing the optimization function, the dose deposition and/or the dose distribution in the planning target volume and the organ at risk can be optimized, e.g. according to the prescribed dose for the planning target volume and/or according to the at least one constraint for the organ at risk. This further allows to determine an optimum set of settings for the medical system and/or the radiation treatment apparatus, which is also referred to as optimization process above and in the following.

According to an embodiment of the invention at least a part of the overlap region of the virtual planning object with the planning target volume is disregarded during the optimization process, in particular during the next iteration of the method. Disregarding this at least a part of the overlap region during the optimization process may mean that the dose deposition in this at least part of the planning target volume is not taken into account for the determination of the optimized dose deposition and/or for the determination of the optimum set of settings of the medical system and/or the radiation treatment apparatus. Therein, disregarding the at least part of the overlap region may comprise flagging this part correspondingly, e.g. based on setting a corresponding flag value.

According to an embodiment of the invention, the method further comprises the step of updating the initial irradiation treatment plan based on the optimized planning target volume, thereby generating an updated irradiation treatment plan.

The updated irradiation treatment may also refer to an optimized irradiation treatment plan. Also, a planning dose delivered to and/or deposited in the optimized planning target volume may be calculated based on the updated (or optimized) irradiation treatment plan. The updated irradiation treatment may also be output, e.g. via a user interface, and/or it may be written to a treatment plan file and/or stored on a data storage device. The updated irradiation treatment plan and/or the treatment plan file can then for example be fed and/or provided to a medical system and/or radiation treatment apparatus to instruct the system and/or apparatus to carry out the irradiation treatment according to the updated (or optimized) irradiation treatment plan. Further, it is noted that alternatively or additionally the optimized planning target volume can be output, e.g. via a user interface. The optimized planning target volume may, for instance, be visualized on the user interface.

According to an embodiment of the invention, the steps of:
  calculating an organ dose deposited in and/or delivered to said at least part and/or partial volume of the organ at risk when applying an initial irradiation treatment plan;
  determining an amount of violation of the at least one constraint based on comparing the at least one constraint and the calculated organ dose;
  calculating a reduction coverage volume for the planning target volume based on the determined amount of violation;
  generating a virtual planning object by changing, e.g. increasing or decreasing, a volume of the organ at risk, such that an overlap region of the virtual planning object with the planning target volume corresponds to the reduction coverage volume; and
  reducing the initial coverage volume of the planning target volume based on removing at least a part of said overlap region from the planning target volume, thereby generating an optimized planning target volume to be irradiated during the irradiation treatment
are repeated in an iteration process, preferably in an automatic, automated and/or fully automated iteration process. Optionally, also the steps of:
  providing an initial coverage volume for a planning target volume to be irradiated in an irradiation treatment with a prescribed dose; and
  providing at least one constraint for an organ at risk, the at least one constraint being indicative of an allowed dose delivered to at least a part and/or a partial volume of the organ at risk may be repeated in the iteration process.

Further, any other step, partial step and/or sub-step, as described above and in the following, can optionally be repeated in the iteration process. Generally, repeating at least some of the steps of the method may advantageously allow to determine an optimum dose distribution in the planning target volume and the organ at risk, e.g. based on iteratively reducing the amount of violation. Thereby, for example, an optimum trade-off between a biologically effective dose deposited in at least a partial volume of the planning target volume, e.g. corresponding to the optimized planning target volume, and the at least one constraint and/or the sparing of the organ at risk may be found. Further, an optimum set of settings of the medical system and/or the radiation treatment apparatus and/or an optimum irradiation treatment plan may be determined via the iteration process.

According to an embodiment of the invention, the method further comprises the steps of:
  calculating, in each iteration of the iteration process, an optimized organ dose delivered to at least a part of the organ at risk; and
  determining an optimized amount of violation of the at least one constraint of the organ at risk based on comparing the at least one constraint and the optimized dose delivered to said at least part of the organ at risk.

In this way, the amount of violation may be iteratively reduced and the iteration process may effectively converge to an optimized planning target volume, in which the amount of violation is minimized and/or in which the at least one constraint is fulfilled.

According to an embodiment of the invention, the iteration process is terminated if the at least one constraint of the organ at risk is fulfilled.

Once the at least one constraint is fulfilled, the optimized planning target volume as well as an optimum trade-off between sparing of the organ at risk and deposition of a biologically effective dose in the planning target volume may be found. Also, an optimum irradiation treatment plan, e.g. comprising an optimum set of setting of the medical system and/or the radiation treatment apparatus, may then be found and/or determined.

According to an embodiment of the invention, the method further comprises the step of providing a voxel representation of at least a part of a patient, wherein the voxel representation comprises the planning target volume and the organ at risk. Alternatively or additionally, the step of reducing the initial coverage volume comprises the partial steps or sub-steps of determining one or more voxels of the planning target volume arranged at least partly in the overlap region of the virtual planning object with the planning target volume, and removing at least a subset of the determined one or more voxels from the planning target volume to generate the optimized planning target volume.

Generally, using a voxel representation of the at least part of the patient allows to precisely determine the (optimized) irradiation treatment plan, as an entire irradiation geometry, including the dose deposition in the patient as well as any set of settings for the medical system and/or the radiation treatment apparatus can be taken into account. The voxel representation may, for example, be retrieved, acquired and/or derived from patient data, e.g. including one or more scans or images of the at least part of the patient, such as e.g. computed tomography images, magnetic resonance images, and/or ultrasound images. It is emphasized, however, that the invention is not limited to such voxel representation. Rather, any suitable representation of the at least part of the patient can be used, such as e.g. a model of the at least part, a standard anatomical model, a slice representation, a two-dimensional representation, finite elements and/or any other representation.

According to an embodiment of the invention, the generation of the virtual planning object comprises isotropically changing, e.g. increasing or decreasing, the volume of the organ at risk in three spatial directions.

In other words, the volume of the organ at risk can be changed, e.g. expanded or shrunk, uniformly in three spatial directions. For instance, the contour, outer surface, perimeter and/or circumference of the organ at risk can be uniformly changed, e.g. expanded or shrunk, in three spatial directions, e.g. using the radius. Isotropically changing, e.g. increasing or decreasing, the organ at risk or the volume thereof to generate the virtual planning object may safe computing-power and/or computing time, thereby potentially accelerating the process of determining the optimized planning target volume.

According to an embodiment of the invention, the generation of the virtual planning object comprises non-isotropically changing, e.g. increasing or decreasing, the volume of the organ at risk in three spatial directions.

In other words, the volume of the organ at risk can be changed, e.g. expanded or shrunk, non-uniformly in three spatial directions. For instance, a part of the contour, outer surface, perimeter and/or circumference of the organ at risk can be increased or decreased by a first margin and other parts of the contour, outer surface, perimeter and/or circumference of the organ at risk can be changed by one or more further margins, differing from the first margin. Accordingly, a shape and/or geometry of the virtual planning object may differ from a shape and/or geometry of the organ at risk due to the non-uniform change of the organ at risk's volume. Non-isotropically changing, e.g. increasing or decreasing, the organ at risk may allow to effectively reduce the planning target volume by removing parts thereof which, when irradiated, may largely affect the organ at risk. Hence, the amount of violation may be effectively reduced when such parts of the planning target volume may be removed.

According to an embodiment of the invention, the step of changing the volume of the organ risk further comprises:
    determining a centre axis intersecting a centre of the organ at risk and a centre of the planning target volume;
    changing, e.g. increasing or decreasing, a size of the organ at risk in a first direction parallel to the centre axis by a first margin; and
    changing, e.g. increasing or decreasing, the size of the organ at risk in a second direction transverse to the centre axis by a second margin.

Therein, the first margin differs from the second margin. Generally, the first margin may refer to a first increment value or a first decrement value. Likewise, the second margin may refer to a second increment value or a second decrement value.

The first margin may be larger or smaller than the second margin. The centre of the organ at risk may refer to a geometric centre and/or a centre of mass of the organ at risk. Likewise, the centre of the planning target volume may refer to a geometric centre and/or a centre of mass of the planning target volume. Based on the first and second margins a shape, extension and/or geometry of the organ at risk with respect to the planning target volume may be taken into account for the determination of the optimized planning target volume.

In a second aspect, the invention is directed to a computer program which, when running on and/or executed by at least one processor of at least one computer or when loaded into at least one memory of at least one computer, causes the at least one computer to perform the method according to the first aspect, as described above and in the following. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect.

A computer program stored on a disc is a data file, and when the file is read out and transmitted it becomes a data stream for example in the form of a (physical, for example electrical, for example technically generated) signal. The signal can be implemented as the signal wave which is described herein. For example, the signal and/or the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer, comprising at least one processor and at least one memory, wherein the program according to the second aspect is running on the processor or is loaded into the memory, or wherein the at least one computer comprises the computer-readable program storage medium according to the third aspect.

In a fifth aspect, the invention is directed to a medical system, comprising:
    a) at least one computer according to the fourth aspect;
    b) at least one electronic data storage device storing patient data, such as e.g. a voxel representation of at least a part of the patient, a clinical protocol file and/or an (optimized) irradiation treatment plan; and
    c) a medical device for carrying out a medical procedure on the patient,
    wherein the at least one computer is operably coupled to
        the at least one electronic data storage device for acquiring and/or retrieving, from the at least one data storage device, at least the patient data, and
        the medical device for issuing a control signal to the medical device for controlling the operation of the medical device on the basis of the optimized planning target volume and/or an optimized irradiation treatment plan, e.g. determined based on the method according to the first aspect.

In an example of the system according to the fifth aspect, the medical device comprises a radiation treatment apparatus comprising a treatment beam source and a patient support unit (such as at least one of a patient bed or a headrest). The at least one computer is then operably coupled to the radiation treatment apparatus for issuing a control signal to the radiation treatment apparatus for controlling, on the basis of the optimized planning target volume and/or the optimized irradiation treatment plan, at least one of the operation of the treatment beam source and the position of the patient support unit.

The present invention also relates to the use of any of the first to fifth aspect. Particularly, the invention also relates to the use of the method according to the first aspect, the program according to the second aspect, the computer-readable medium according to the third aspect and/or the computer according to the fourth aspect in the medical system or any embodiment thereof according to the fifth aspect.

Moreover, it is emphasized that features, functions, elements and/or steps, which are described above and in the following with reference to one aspect of the invention, equally apply to any other aspect of the invention described above and in the following. Particularly, features and/or steps, as described above and in the following, with reference to the method according to the first aspect, equally apply the computer program according to the second aspect, to the computer-readable medium according to the third aspect, to the computer according to the fourth aspect and/or to the medical system according to the fifth aspect, and vice versa.

These and other aspects of the invention will be apparent from and elucidated with reference to the embodiments described hereinafter.

Definitions

In this section, definitions for specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp)

and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

According to the present disclosure the terms acquiring data and retrieving data may be used synonymously. The expression "acquiring data" or "retrieving data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Shape Representatives

Shape representatives and/or representations represent a characteristic aspect of the shape of an anatomical structure. Examples of shape representatives include straight lines, planes and geometric figures. Geometric figures can be one-dimensional such as for example axes or circular arcs, two-dimensional such as for example polygons and circles, or three-dimensional such as for example cuboids, cylinders and spheres. The relative position between the shape representatives can be described in reference systems, for example by co-ordinates or vectors, or can be described by geometric variables such as for example length, angle, area, volume and proportions. The characteristic aspects which are represented by the shape representatives are for example symmetry properties which are represented for example by a plane of symmetry. Another example of a characteristic aspect is the direction of extension of the anatomical structure, which is for example represented by a longitudinal axis. Another example of a characteristic aspect is the cross-sectional shape of an anatomical structure, which is for example represented by an ellipse. Another example of a characteristic aspect is the surface shape of a part of the anatomical structure, which is for example represented by a plane or a hemisphere. For example, the characteristic aspect constitutes an abstraction of the actual shape or an abstraction of a property of the actual shape (such as for example its symmetry properties or longitudinal extension). The shape representative for example represents this abstraction.

Atlas/Atlas Segmentation

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionizing radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/health-care_us_elekta_vmat.php and http://www.varian.com/us/oncology/treatments/treatment_techniques/rapidarc.

Arrangement of Treatment Beams

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

BRIEF DESCRIPTION OF THE DRAWINGS

In the following, the invention is described with reference to the appended figures which give background explanations and represent exemplary embodiments of the invention. The scope of the invention is however not limited to the specific features disclosed in the context of the figures, wherein.

The figures are schematic only and not true to scale. In principle, identical or like parts, elements and/or steps are provided with identical or like reference symbols in the figures.

DESCRIPTION OF EMBODIMENTS

Figure 1:
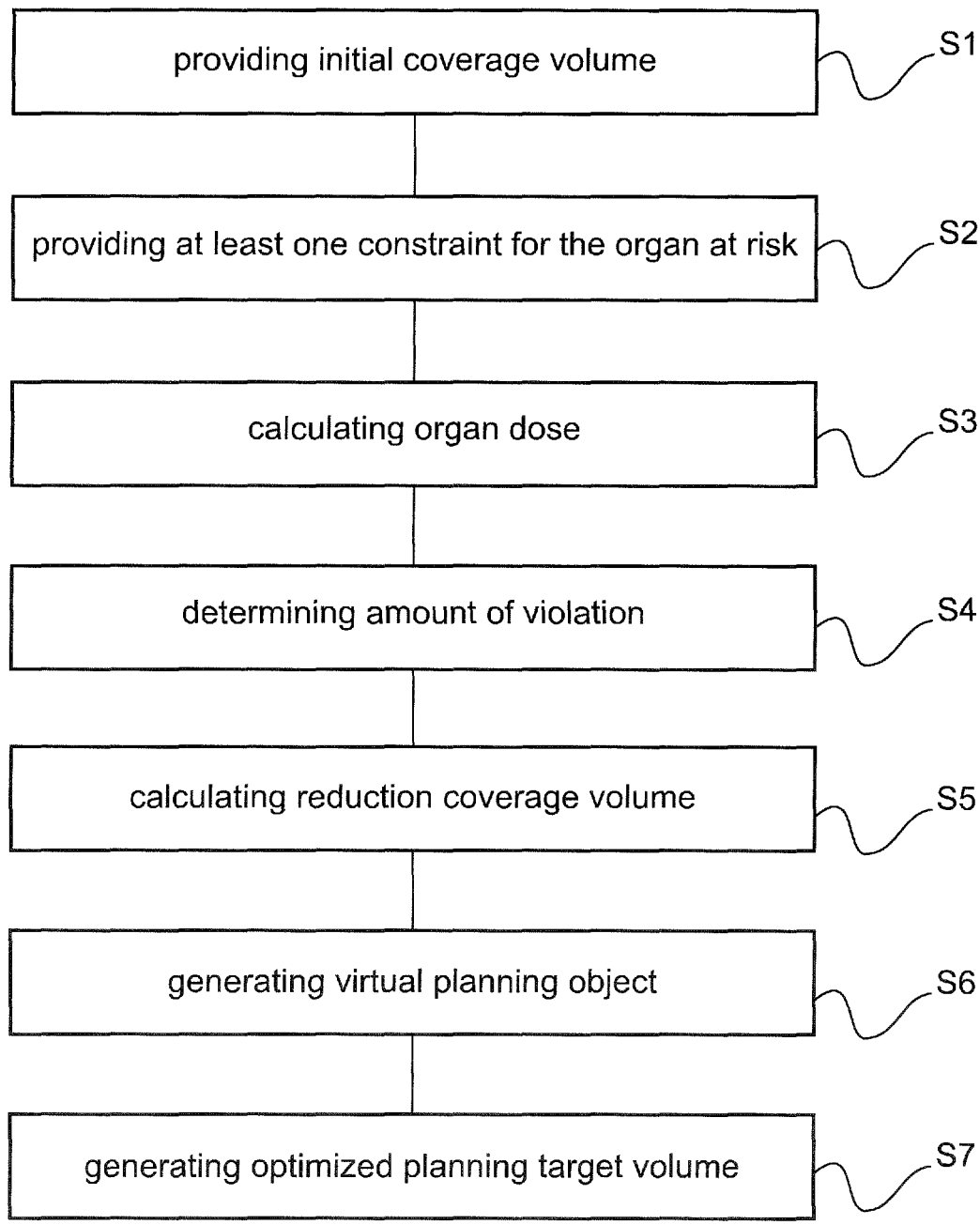
FIG. 1 shows a flowchart illustrating steps of a method of irradiation treatment planning according to an exemplary embodiment of the invention.

FIG. 1 shows a flow chart illustrating the basic steps of the method of irradiation treatment planning according to an exemplary embodiment and/or according to the first aspect. Step S1 comprises providing an initial coverage volume for a planning target volume to be irradiated in an irradiation treatment with a prescribed dose. Step S2 comprises providing at least one constraint for an organ at risk, the at least one constraint being indicative of an allowed dose deposited in at least a part or partial volume of the organ at risk. In a further step S3 an organ dose deposited in said at least part or partial volume of the organ at risk is calculated, when applying an initial irradiation treatment plan and/or according to the initial irradiation treatment plan. Further, step S4 comprises determining an amount of violation of the at least one constraint based on comparing the at least one constraint and the calculated organ dose, Step S5 comprises calculating a reduction coverage volume for the planning target volume based on the determined amount of violation. In step S6, a virtual planning object is generated by changing, e.g. increasing or decreasing, a volume of the organ at risk, such that an overlap region of the virtual planning object with the planning target volume corresponds to the reduction coverage volume. Therein, step S6 may comprise determining the overlap region. Moreover, step S7 comprises generating an optimized planning target volume to be irradiated during the irradiation treatment based on and/or by reducing the initial coverage volume of the planning target volume based on and/or by removing at least a part of said overlap region from the planning target volume.

With the method described in FIG. 1, an optimum trade-off between a biologically effective dose deposited in at least a partial volume of the planning target volume, e.g. corresponding to the optimized planning target volume, and the at least one constraint and/or the sparing of the organ at risk may be found. Further, an optimum set of settings of the medical system and/or the radiation treatment apparatus and/or an optimum irradiation treatment plan may be determined via the iteration process. This will be explained in more detail in the context of the following Figures. At least some of the steps described above with reference to FIG. 1, partial steps thereof, sub-steps thereof, and/or further optional steps will be described in more detail with reference to FIGS. 3A to 3E.

Figure 2A:
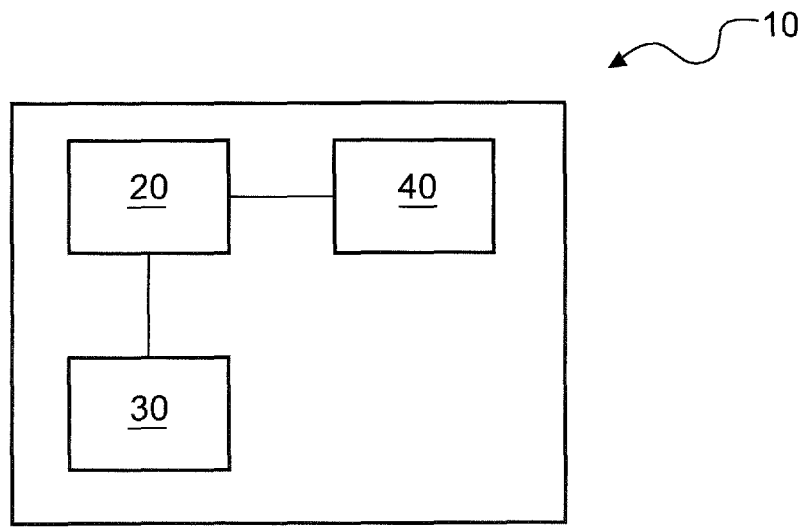
FIG. 2A schematically shows a medical system according to an exemplary embodiment of the invention.

FIG. 2A shows schematically a medical system 10 according to an exemplary embodiment of the invention and/or according to the fifth aspect. The system is in its entirety identified by reference numeral 10 and comprises a computer 20, an electronic data storage device (such as a hard disc) 30 for storing at least patient data, and a medical device 40, e.g. for carrying out a medical procedure, particularly an irradiation treatment. The components of the medical system 10 have the functionalities and properties explained above and in the following with regard to the fifth and/or any other aspect of the present disclosure. Particularly, the at least one computer 20 is operably coupled to the at least one electronic data storage 30 device for acquiring, from the at least one data storage device 30, at least the patient data. Further, computer 20 is coupled to the medical device 40 for issuing a control signal to the medical device 40 for controlling the operation of the medical device 40 on the basis of the generated optimized planning target volume, as described above and in the following.

Figure 2B:
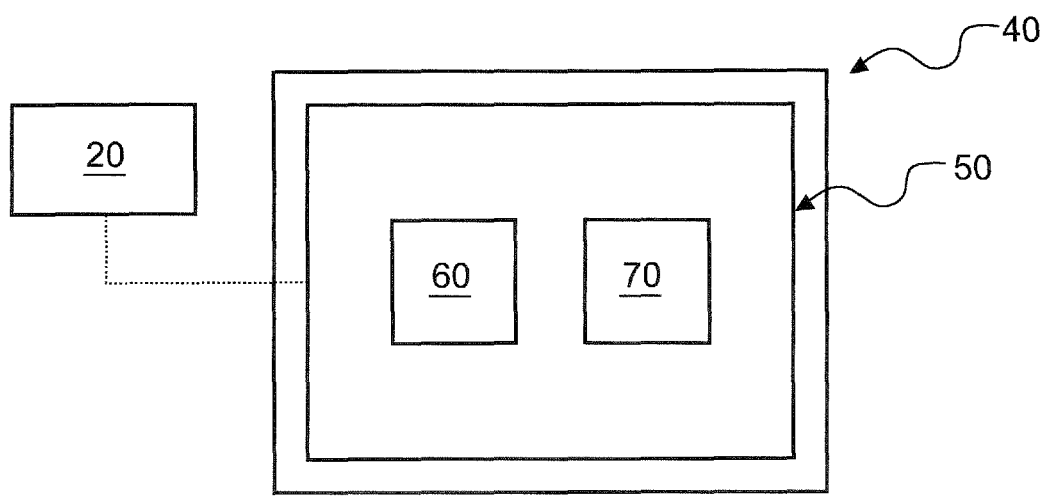
FIG. 2B schematically shows a medical device of the medical system of FIG. 2A.

FIG. 2B schematically shows a medical device 40 of the medical system 10 of FIG. 2A. The medical device 40 comprises a radiation treatment apparatus 50 comprising a treatment beam source 60 and a patient support unit 70, wherein the at least one computer 20 is operably coupled to the radiation treatment apparatus 50 for issuing a control signal to the radiation treatment apparatus 50 for controlling, on the basis of the generated optimized planning target volume, at least one of the operation of the treatment beam source 60 and the position of the patient support unit 70.

Figure 3A:
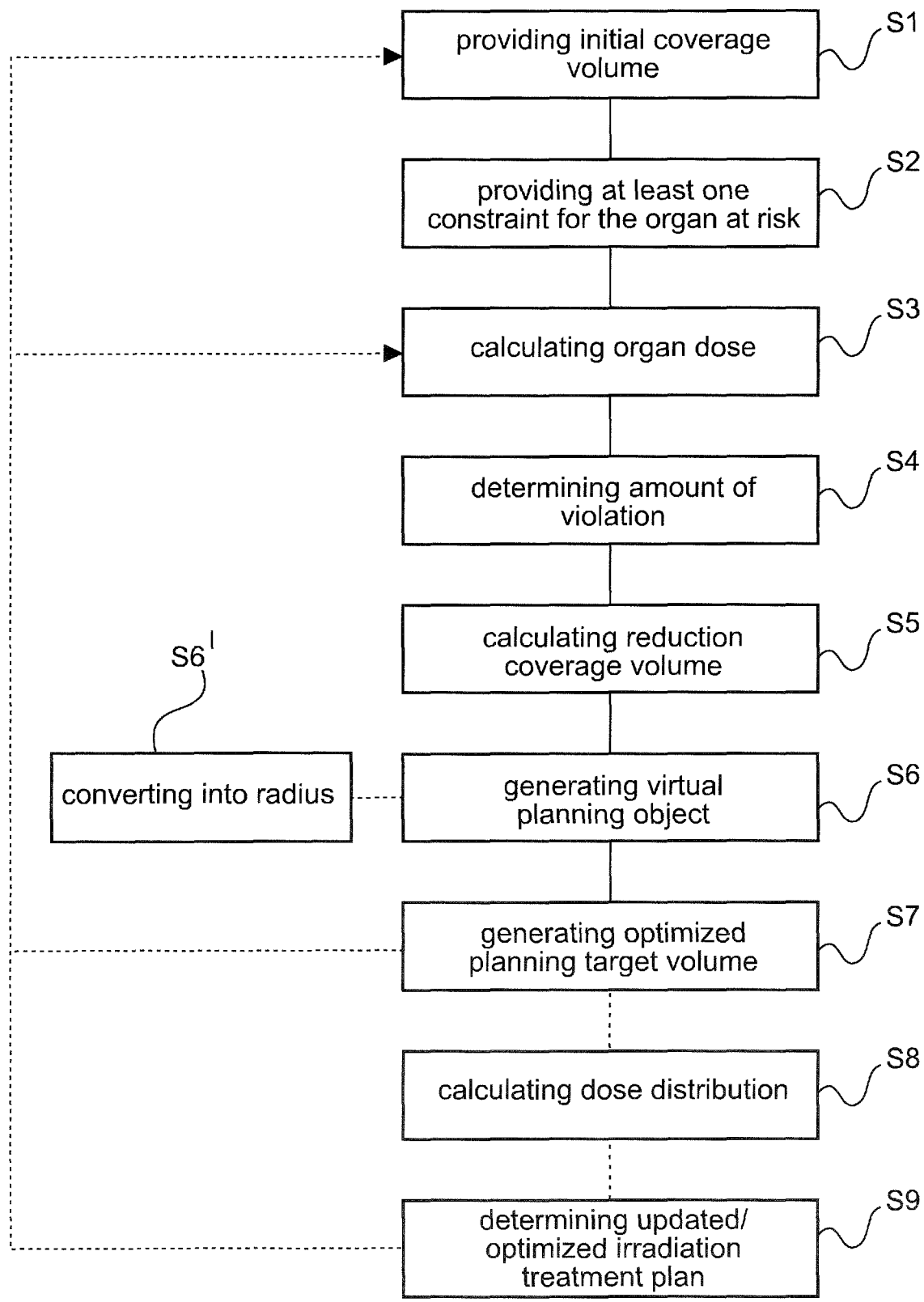
FIG. 3A shows a flow chart illustrating steps of a method of irradiation treatment planning according to another exemplary embodiment of the invention.
Figure 3B:
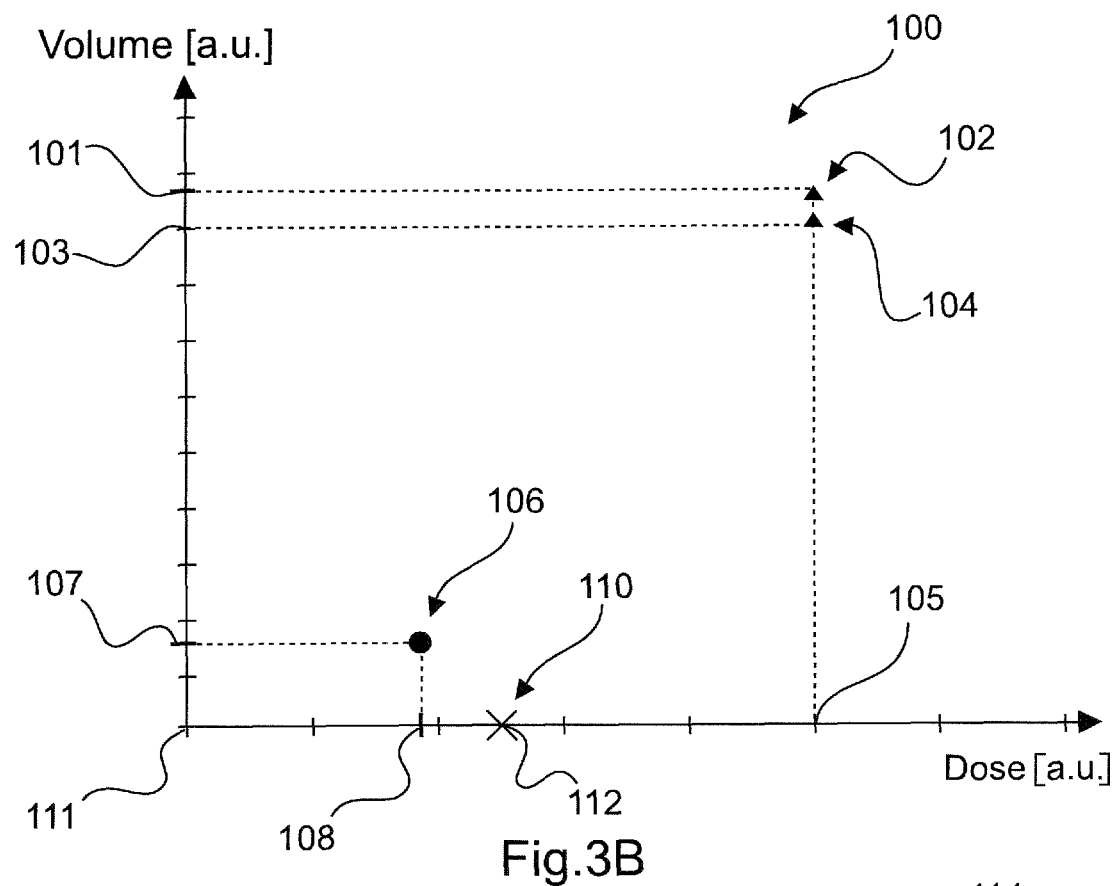
FIG. 3B shows an exemplary dose volume histogram illustrating one or more steps of the method of FIG. 3A.
Figure 3C:
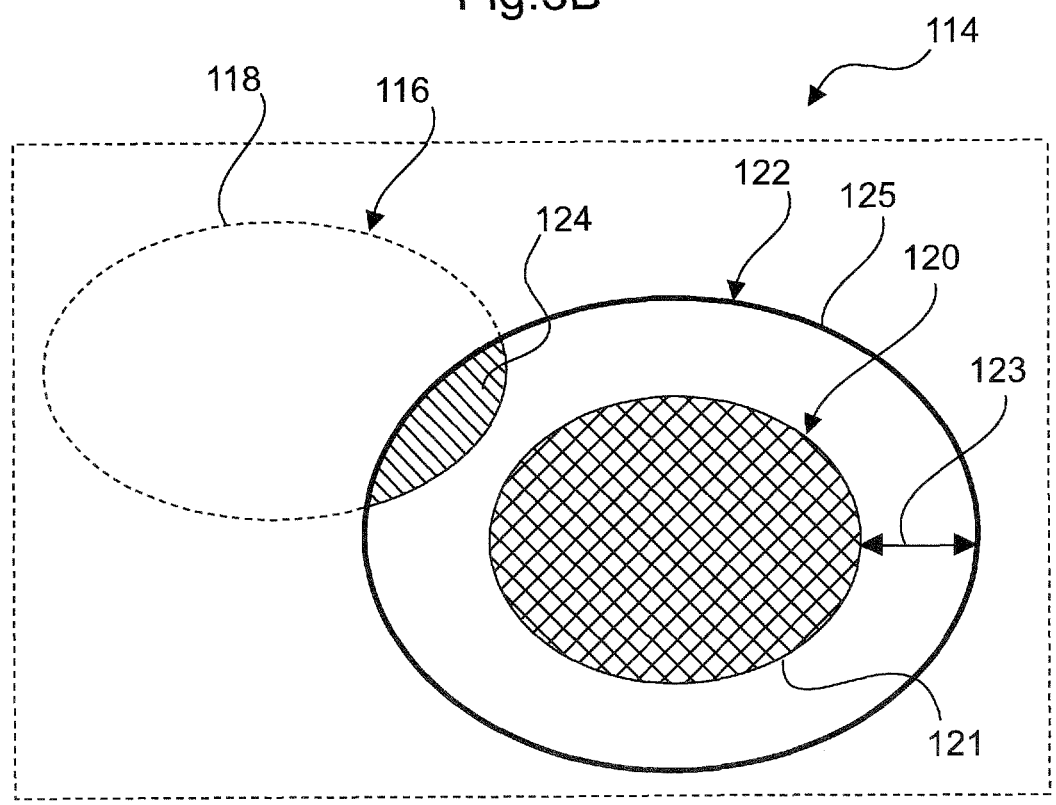
FIGS. 3C to 3E show a representation of a part of a patient to illustrate one or more steps of the method of FIG. 3A.
Figure 3D:
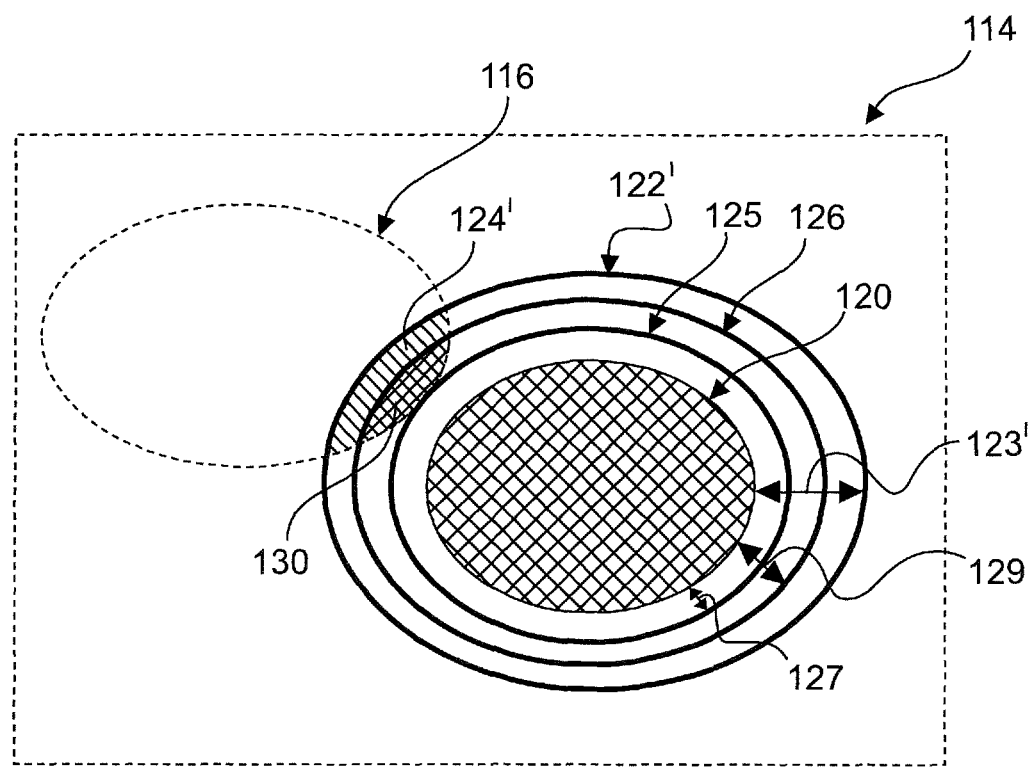
Figure 3E:
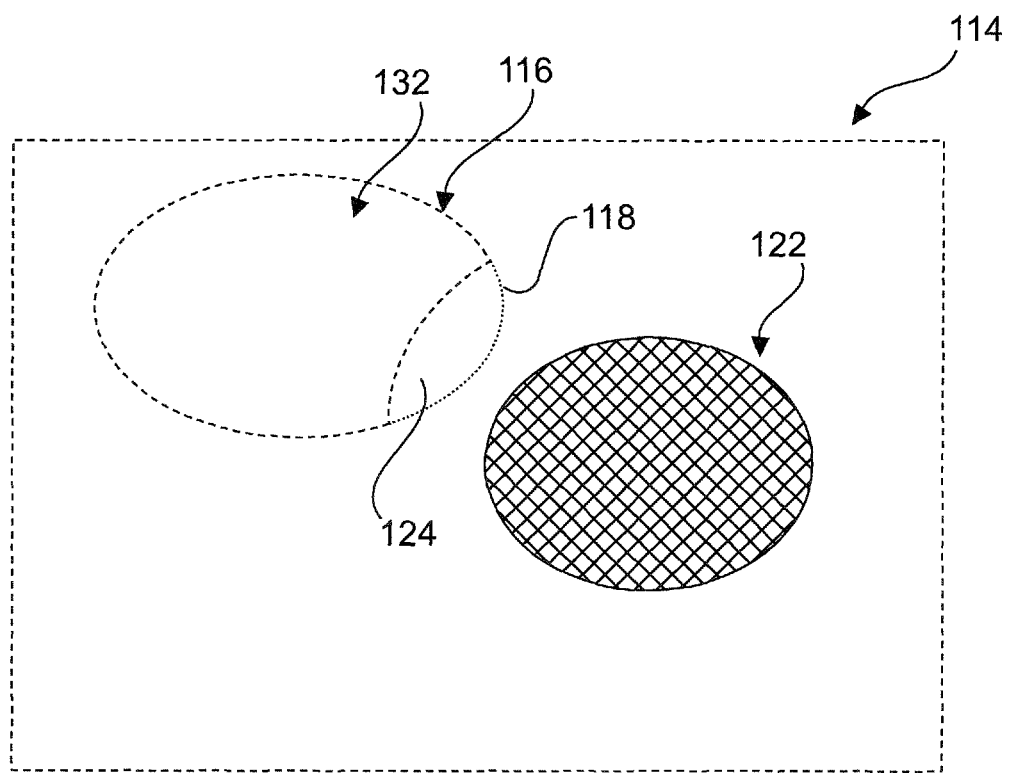

FIG. 3A shows a flow chart illustrating steps of a method of irradiation treatment planning according to another exemplary embodiment of the invention. If not stated otherwise, the method described with reference to FIG. 3A comprises the same steps as the method described with reference to FIG. 1. FIG. 3B shows an exemplary and/or cumulative dose volume histogram 100 illustrating one or more steps of the method of FIG. 3A. FIGS. 3C to 3E each show a representation of a part of a patient, thereby illustrating one or more steps of the method of FIG. 3A.

Specifically, FIG. 3C (and similarly FIGS. 3D and 3E) illustrates a representation 114 of a part of a patient and/or a part 114 of an anatomical structure of a patient. The illustrated part 114 and/or representation 114 comprises the planning target volume 116, which is to be irradiated in the irradiation treatment and/or for which an irradiation treatment plan is to be determined. The planning target volume 116 may be a representation of e.g. a tumour, a metastasis, cancerous tissue and/or any other tissue of the patient to be treated. The part 114 of the patient further comprises the organ at risk 120, which may be a representation of any vital organ of the patient, such as e.g. a brainstem, an eye, an eye nerve, and/or any other tissue that might be relevant for a vital function of the patient. The representation of the part 114 of the patient may, for instance be a voxel representation 114, exemplary illustrated two-dimensionally in FIGS. 3C to 3E, or any other representation 114.

Further, FIG. 3B shows a dose volume histogram 100. Specifically, FIG. 3B shows a volume (absolute or relative) of a planning target volume 116 and/or the organ at risk 120 in arbitrary units as a function of the dose deposited therein in arbitrary units. Generally, the dose volume histogram 100 shows the dose that a certain partial volume (e.g. a percentage) of a given volume (e.g. the planning target volume 116 and/or the organ at risk 120) receives, or more.

In the following, it may be referred to any of FIGS. 3A to 3E.

Referring to FIG. 3A, step S1 comprises providing an initial coverage volume 118 for the planning target volume 116 to be irradiated in the irradiation treatment with a prescribed dose 105. As illustrated in FIG. 3C, the initial coverage volume 118 may comprise and/or refer to the entire planning target volume 116. However, the initial coverage volume 118 may alternatively be any partial volume 118 of the planning target volume 116. The initial planning target volume 118 may, for instance, be provided via user input and/or it may be retrieved or acquired from the data storage device 40. By way of example, the data storage device 40 may store a clinical protocol file, in which the initial coverage volume 107 may be specified. The clinical protocol file can, for instance, be defined and/or selected by a user, such as a user of the medical system 10, the medical device 40 and/or the radiation treatment apparatus 50.

The clinical protocol file and/or one or more data elements or entries thereof may contain information related to a dose volume histogram 100, as exemplary illustrated in FIG. 3B. From the user input and/or from the data storage device 40, e.g. an input value 102 comprising and/or specifying a desired coverage volume 101 may be retrieved, as indicated in the dose volume histogram 100 of FIG. 3B. The desired coverage volume 101 may refer to the volume of the planning target volume 116, in which preferably a prescribed dose 105 is deposited during the irradiation treatment, e.g. in order to ensure biological effectiveness of the treatment. Accordingly, the input value 102 may be indicative of an accumulated prescribed dose 105 deposited in the partial volume 101 and/or the desired coverage volume 101.

The desired coverage volume 101 may be selected in step S1 as the initial coverage volume 118. Alternatively, any other partial volume of the planning target volume 116 may be selected as the initial coverage volume 118 in step S1. Accordingly, step S1 may, optionally, comprise retrieving, receiving and/or providing the desired coverage volume 101, e.g. based on receiving the input value 102.

Step S1 can, optionally, comprise retrieving, receiving and/or providing a tolerated coverage volume 103 of the planning target volume 116, wherein the tolerated coverage volume 103 is indicative of a minimum volume or partial volume of the planning target volume 116, in which a prescribed dose 105 should be deposited to ensure biological effectiveness. The tolerated coverage volume 103 and/or the corresponding accumulated and/or prescribed dose 105, analogue to the desired coverage volume 101, may be provided as input value 104, e.g. via user input, via the clinical protocol file and/or via the data storage device 40. The input value 104 may be indicative of an accumulated prescribed dose 105 deposited in the partial volume 103 of the planning target volume 116. It is noted that the prescribed dose 105 for the tolerated coverage volume 103 can differ from the prescribed dose 105 of the desired coverage volume 101.

Generally, the input values 102, 104, the desired coverage volume 101, the tolerated coverage volume 103 and/or the prescribed dose 105 can be regarded as coverage volume and/or dose wishes, which can be read from the clinical protocol file, e.g. defined by the user, which typically is the medical practitioner.

Optionally, step S1 may comprise retrieving, receiving, acquiring, and/or providing the representation 114, e.g. the voxel representation 114. The representation 114 may e.g. be retrieved and/or acquired from patient data stored on e.g. the data storage device 40.

Moreover, the planning target volume 116 in the representation 114 may, optionally, be drawn by a user in step S1. Further, the organ at risk 120 may be auto-segmented, e.g. based on atlas or atlas segmentation, or manually drawn by the user in step S1.

Apart from that, step S1 may comprise visualizing the representation 114, the planning target volume 116, the initial coverage volume 118, and/or the organ at risk 120, e.g. on a user interface of the medical system 10. Moreover, one or both input values 102, 104 may be visualized, e.g. based on iso-dose lines and/or iso-dose curves.

Step S2 comprises providing at least one constraint 106, 110, wherein the at least one constraint 106, 110 is indicative of an allowed dose 108, 112 deposited in at least a part 107, 111 or a partial volume 107, 111 of the organ at risk 120. As illustrated in FIG. 3B, the at least one constraint 106, 110 may be provided via one or more input values 106, 110, e.g. via a user input and/or via the data storage device 40. The input values 106, 110 may be provided, analogue to the input values 102, 104, e.g. via a clinical protocol file. Exemplary, input value 106 (or constraint 106) refers to a maximum accumulated dose 108 deposited in a partial volume 107 of the organ at risk 120. Further, input value 110 (or constraint 110) refers to a maximum dose 112 which should be deposited in a volume 111 of size zero of the organ at risk 120, i.e. in no partial volume of the organ at risk 120. The dose values 108, 112, each may refer to an allowed dose 108, 112 deposited in at least a partial volume 107, 110 of the organ at risk 120, as indicated by the at least one constraint 106, 110. Any one or both of the input values 106, 110 may be selected, preferably automatically, as constraint or constraints 106, 110 for the organ at risk 120 in step S2.

Moreover, a most important organ at risk 120 may be specified, e.g. in the clinical protocol file and/or via a user input. This most important organ at risk 120 may then be treated with highest priority during the method of irradiation treatment planning, exemplarily illustrated in FIG. 3A. Accordingly, step S2 may optionally comprise determining and/or selecting the most important organ at risk 120 and/or at least one constraint 106, 110 associated therewith. It is emphasized that also one or more further organs at risk and/or one or more further constraints can be provided in step S2.

In step S3 an organ dose deposited in at least a part or partial volume of the organ at risk 120 is calculated, when applying an initial irradiation treatment plan and/or according to the initial irradiation treatment plan. The part or partial volume of the organ at risk 120 may refer to the volume 107 and/or 111, as indicated and/or specified by the at least one constraint 106, 110. The organ dose can e.g. be calculated based on a simulation or simulation calculation. For instance, a set of settings for the medical system 10 and/or the medical device 40 can be provided in the initial irradiation treatment plan, based on which set of settings the organ dose can be calculated.

Further, step S4 comprises determining an amount of violation of the at least one constraint 106, 110 based on comparing the at least one constraint 106, 110 and the calculated organ dose. If a plurality of constraints 106, 110 is taken into account, a plurality of amounts of violation may be determined in step S4, i.e. an amount of violation for each constraint 106, 110 may be determined. Comparing the at least one constraint 106, 110 and the calculated organ dose may optionally comprise subtracting the calculated organ dose and the at least one constraint 106, 110 (and/or the allowed dose 108, 112 indicated by the at least one constraint 106, 110). Also, a ratio of the organ dose and the at least one constraint 106, 110 (and/or the allowed dose 108, 112) may be determined in step S4. For example, the amount of violation may be given for each constraint 106, 110 and/or organ at risk 120 as an excessive dose, exceeding the respective allowed dose 108, 112, as indicated by the respective constraint 106, 110. The determined amount of violation may, optionally, be output in step S4, e.g. on a user interface.

Step S5 comprises calculating a reduction coverage volume for the planning target volume 116 based on the amount of violation determined in step S4. Also, the tolerated coverage volume 103, e.g. as indicated by input value 104, may be taken into account for the determination of the reduction coverage volume. For instance, the reduction coverage volume may be determined as a function of the amount of violation and the tolerated coverage volume 103. The reduction coverage volume may e.g. correlate with a product of the tolerated coverage volume 103 and the amount of violation. Also one or more further parameters and/or variables can be taken into account for the determination of the reduction coverage volume.

In step S6, a virtual planning object 122 is generated by or based on changing, varying, modifying and/or adjusting a volume of the organ at risk 120, such that an overlap region 124 or overlap volume 124 of the virtual planning object 122 with the planning target volume 116 corresponds to the reduction coverage volume, as calculated in step S5. Therein, step S6 may comprise determining the overlap region 124. The volume of the organ at risk 120 may be isotropically or non-isotropically changed to generate the virtual planning object 122. Therein, the volume of the organ at risk 120 may be increased and/or the organ at risk 120 may be expanded in order to generate the virtual planning object 122. Alternatively, the volume of the organ at risk may be decreased (and/or reduced) and/or the organ at risk 120 may be shrunk in order to generate the virtual planning object 122.

Step S6 may comprise the optional step S6' of converting and/or translating the reduction coverage volume into a radius 123 of the virtual planning object 122. As indicated by the arrow 123 in FIG. 3C, the radius 123 may refer to a margin, such as e.g. an increment value, by which a contour, outer surface, perimeter and/or circumference 121 of the organ at risk 120 is expanded and/or increased to generate the virtual planning object 122. Alternatively, the radius may refer to a margin, such as e.g. a decrement value, by which the contour, outer surface, perimeter and/or circumference 121 of the organ at risk 120 is decreased, reduced and/or shrunk to generate the virtual planning object 122. Accordingly, the radius 123 may refer to a distance between the contour, outer surface, perimeter and/or circumference 121 of the organ at risk 120 and an outer surface, contour, perimeter and/or circumference 125 of the virtual planning object 122.

The radius 123 may for instance be determined based on a list or look-up table comprising a plurality of pairs of entries, each pair of entries specifying a radius 123', 127, 129 of an auxiliary planning object 122', 126, 128 and an amount of overlap 124', 130 of the corresponding auxiliary planning object 122', 126, 128 and the planning target volume 116. The auxiliary planning objects 122', 126, 128, the corresponding radii 123', 127, 129 and the amounts of overlap 124', 130 are illustrated in FIG. 3D. By way of example, in step S6 and/or step S6' the list may be searched and the auxiliary planning object 122', having an amount of overlap 124' matching and/or substantially corresponding to the previously calculated reduction coverage volume may be selected and the corresponding radius 123' of this auxiliary planning object 122' may selected as the virtual planning object 122, e.g. as depicted in FIG. 3C.

Alternatively or additionally, a plurality of the pairs of entries of the list may be interpolated, e.g. linearly interpolated, in order to determine the radius 123 of the virtual planning object 122, such that the overlap region 124 corresponds to the determined reduction coverage volume.

Optionally, in step S6' the list of pairs of entries may be generated based on generating the plurality of auxiliary planning objects 122', 126, 128, determining the corresponding radii 123', 127, 129 and the associated amounts of overlap 124', 130.

Further, step S7 comprises generating an optimized planning target volume 132 to be irradiated during the irradiation treatment based on and/or by reducing the initial coverage volume 118 of the planning target volume 116 based on and/or by removing at least a part of the overlap region 124 from the planning target volume 116. The optimized planning target volume 132 is illustrated in FIG. 3E.

Optionally, e.g. if the representation 114 is a voxel representation 114, step S7 may comprise determining one or more voxels of the planning target volume 116, which are at least partly located and/or arranged in the overlap region 124, and removing at least some of and/or a subset of these voxels from the planning target volume 116 to generate the optimized planning target volume 132. Optionally, the optimized planning target volume 132 may be output and/or visualized in step S7, e.g. via an output on the user interface.

In an optional step S8, a dose distribution for at least a part of the planning target volume 116 and at least a part of the organ at risk 120 may be calculated based on an optimization function, wherein at least a part of the overlap region 124 of the virtual planning object 122 with the planning target volume 116 is disregarded in the calculation of the dose distribution. Particularly, the part removed from the planning target volume 116 to generate the optimized planning target volume 132 can be disregarded.

In a further optional step S9 an updated and/or optimized irradiation treatment plan may be determined. For the determination of the updated or optimized irradiation treatment plan the optimization function may be minimized. Therein, the optimization function may describe a deviation of a specified dose and the dose or dose distribution calculated in step S8, when using a current set of settings for the medical system and/or the radiation treatment apparatus (e.g. according to the initial irradiation treatment plan). For the planning target volume 116, the specified dose of the optimization function may relate to the prescribed dose 105, whereas for the organ at risk 120 the specified dose may relate to the one or both allowed doses 108, 112 according to the one or more constraints 106, 110. The set of settings for the medical system 10 and/or the radiation treatment apparatus 50 taken into account for minimizing/maximizing the optimization function may, among others, comprise and/or relate to a particle energy and/or energy distribution of the radiation beam, a fluence rate of the beam, a flux of the beam, an intensity of the beam, one or more settings for a collimator and/or collimator leaves, a collimator shape, and/or any other parameter value related to the actual irradiation treatment. By minimizing/maximizing the optimization function, the dose deposition and/or the dose distribution in the planning target volume 116 and the organ at risk 120 can be optimized, e.g. according to the prescribed dose 105 for the planning target volume 116 and/or according to the at least one constraint 106, 110 (or the allowed doses 107, 111 indicated therein) for the organ at risk 122. This allows to determine an optimum set of settings for the medical system 10 and/or the radiation treatment apparatus 50.

Optionally, the optimum set of settings may then be compiled and/or incorporated into the updated or optimized irradiation treatment plan. The updated or optimized irradiation treatment plan can then e.g. be stored on the data storage device 40. Further, the updated or optimized irradiation treatment plan can then be provided to the medical system 10 or the medical device 40 to carry out the actual irradiation treatment.

In step S8 and/or S9 the at least part of the overlap region 124 of the virtual planning object 122 with the planning target volume 116, which has been removed from the planning target volume 116 to generate the optimized planning target volume 132, can be disregarded, which may mean that the dose deposition in this at least part of the planning target volume may not be taken into account for the determination of the optimum set of settings of the medical system 10 and/or for the minimization/maximization of the optimization function. Accordingly, the at least part of the overlap region 124, which is removed from the planning target volume may e.g. be flagged in any of steps S6 to S9, e.g. based on setting a corresponding flag value.

It is to be noted that in order to find and/or determine the optimized irradiation treatment plan, one or more steps of the method as described with reference to FIGS. 3A to 3E may be repeated in an iteration process, as indicated by the dashed arrows in FIG. 3A. Particularly, steps S3 to S7 may be repeated in the iteration process. However, also steps S1 to S7 may be repeated. Moreover, also at least one of the optional steps S6', S8 and/or S9 may be repeated.

During the iteration process, the reduction coverage volume may be updated in each iteration step, wherein the amount of violation may be iteratively reduced. Accordingly, also the optimized planning target volume 132 may be updated in each iteration step. The iteration may be terminated if the amount of violation reaches a minimum and/or equals zero, thereby indicating that the at least one constraint 106, 110 is fulfilled. Hence, the iteration may be terminated, if the optimum trade-off or compromise between the optimized planning target volume 132 (or a dose deposition in the planning target volume 116) and the at least one constraint 106, 110 is found.

In the following, various examples, elements and/or features of the invention are summarized, which are combinable, alone or in combination, with any embodiment and aspect of the present invention described herein. Generally, dealing with organs at risk 120, which may be located close to, overlap with the planning target volume 116 and/or be affected otherwise by an irradiation of the planning target volume 116, may be a challenging planning task in irradiation treatment planning. In certain scenarios, it may not be possible to fulfil both depositing a prescribed dose 105 in the desired coverage volume 101 and the one or more constraints 106, 110 for the organ at risk 120. Instead, the optimum compromise between these two contradicting goals may have to be found. Also, in certain scenarios the one or more constraints 106, 110 may have to be relaxed, e.g. with side effects that might be tolerable in those scenarios. Alternatively or additionally, the coverage volume, e.g. the desired coverage volume 101, may be relaxed. Under most circumstances or in many scenarios, however, the optimization process for the irradiation treatment planning may guarantee a certain coverage, e.g. given by the desired coverage volume 101 or in the range between tolerated and desired coverage volumes 101, 103.

According to the present disclosure, the coverage volume of the planning target volume 116 may be slowly reduced from the initial coverage volume 118, which may correspond to the desired coverage volume 101, down to a minimum coverage, which may be the tolerated coverage volume 103, if the one or more constraints 106, 110 cannot be fulfilled otherwise. Particularly, this might be the case for the most important organ at risk 120, which may be specified by the user and/or via the clinical protocol file. The one or more constraint 106, 110 of the most important organ at risk 120 may be set to "strict". In certain scenarios, these constraints 106, 110 may not be fulfilled, unless the coverage volume of the planning target volume 116 is significantly reduced. How much the coverage is reduced may depend on the amount of violation of the one or more constraints 106, 110. These features can be part of any embodiment and aspect.

Also, a weight indicative for an importance of the organ at risk 120 and/or a weight indicative for importance of a maximized coverage volume of the planning target volume 116 may be taken into account. These weights may, for example, be specified by the user using one or more weighting sliders. Accordingly, the determination of the optimized planning target volume 132 may be based on a position of the one or more weighting sliders accessible to the user, via e.g. a graphical user interface.

Preferably, for the planning target volume 116 no reduction in coverage volume would be desirable to deposit a maximum dose in a maximum partial volume of (or the entire) the planning target volume 116. On the other hand, for the organ at risk 120 a maximum reduction of the planning target volume 116 may be desirable, e.g. down to the tolerated coverage volume 103, if the one or more constraints 106, 110 for the organ at risk 120 cannot be fulfilled otherwise.

According to the present disclosure, the coverage volume of the planning target volume 116 may not be reduced for the whole planning target volume 116, e.g. independent of locations of the voxels of the planning target volume 116, but location based information may be used in order to make sure the coverage is "sacrificed" at the right location, such as e.g. close to the organ at risk 120. This may be done or accomplished by utilizing the virtual planning object 122, e.g. in combination with and/or based on a series of auxiliary planning objects 122', 126, 128. Therein, the virtual planning object 122 and/or the auxiliary planning objects 122', 126, 128 may refer to an object, which may be generated based on changing, e.g. increasing or decreasing, the volume of the organ at risk 120 and which may or may not be invisible to the user. The virtual planning object 122 and/or the auxiliary planning objects 122', 126, 128 may be automatically created by changing, e.g. expanding or shrinking, the organ at risk 120, e.g. uniformly into all directions. The virtual planning object 120 and/or the auxiliary planning objects 122', 126, 128 may generally be referred to as "virtual objects". For example a virtual object could be created for a radius of 2 mm. This may mean that the virtual object is 2 mm larger than the organ at risk 120.

The concrete virtual object 122 and/or the virtual planning object 122 may be deduced from the amount of "sacrificed" coverage in the following way. First the amount of volume of the planning target volume 116 "sacrificed" is calculated, which may refer to the reduction coverage volume. If e.g. instead of 98% coverage only 96% coverage shall be achieved, effectively 2% of the volume of the planning target volume 116 may be "sacrificed". Now a virtual object and/or the virtual planning object 122 may be created that covers substantially, preferably exactly, the amount of "sacrificed" volume of the planning target volume 116 and/or the reduction coverage volume (e.g. 2%). This means the virtual object and/or virtual planning object 122 may be bigger for larger volume reductions of the planning target volume 116. For example, one or more voxels of the planning target volume 116 which may at least partly be covered by the virtual object 122 will then be marked as "to be sacrificed" for the optimization. These voxels may not have to fulfil the desired dose 105 or prescribed dose 105 for the planning target volume 116.

As described above, according to an embodiment of the invention, one or more input values 102, 104, for the desired and tolerated coverage volumes 101, 103 may be received, e.g. from the clinical protocol file. Further, one or more input values 106, 110, for the one or more constraints 106, 110 may be received, e.g. from the clinical protocol file. Further, a physical dose distribution may be calculated based on the current or initial treatment plan. Moreover, the voxel representation 114 of both the planning target volume 116 and the organ at risk 120 may be received and/or provided.

During determination of the optimized planning target volume 132, the amount of coverage reduction and/or the reduction coverage volume might be updated multiple times throughout the optimization process. Therefore, the virtual object 122 and/or the virtual planning object 122 might also be updated and/or changed multiple times.

The invention advantageously allows, e.g. based on marking or flagging certain voxels as "to be sacrificed", to determine which voxels shall be chosen when reducing the coverage volume of the planning target volume 116. This may prevent bad compromises like reducing the coverage volume of the planning target volume 116 by voxels which are far away from any organ at risk 120.

With planning tools lacking such automatic generation of the virtual object 122 and/or the virtual planning object 122, it may typically be necessary to manually create helping structures. In contrast thereto, the invention advantageously allows the automation, a faster treatment planning process, and the guarantee that the virtual planning object 122 may have exactly the right size that fits to the allowed "sacrifice" or reduction coverage volume of the planning target volume 116. In turn, this may offer a precise control over the compromise between coverage volume of the planning target volume 116 and the sparing of the organ at risk 120.

It is further noted, that the virtual objects 122, 126, 128, the virtual planning object 122, and/or the auxiliary planning objects 122, 126, 128 may be generated via 3D image dilation, e.g. blowing up of the organ at risk 120 uniformly in all three dimensions. Alternatively, the virtual objects 122, 126, 128, the virtual planning object 122, and/or the auxiliary planning objects 122, 126, 128 may be generated differently. E.g. the direction that is given by the centre of mass axis through the centre of mass of the planning target volume 116 and the centre of mass of the organ at risk 120 could be treated differently than other directions. For instance, the virtual objects 122, 126, 128, the virtual planning object 122, and/or the auxiliary planning objects 122, 126, 128 could be generated by changing, e.g. increasing or decreasing, the volume of the organ at risk 120 more in this direction and less in other directions, or vice versa. Hence, the virtual objects 122, 126, 128, the virtual planning object 122, and/or the auxiliary planning objects 122, 126, 128 can be generated based on a non-uniform and/or non-isotropic change, e.g. expansion or reduction (shrinkage), of the organ at risk 120.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method of irradiation treatment planning, the method comprising:

providing an initial coverage volume for a planning target volume to be irradiated in an irradiation treatment with a prescribed dose;

providing at least one constraint for an organ at risk, the at least one constraint being indicative of an allowed dose deposited in at least a part of the organ at risk;

calculating an organ dose deposited in said at least part of the organ at risk based on applying an initial irradiation treatment plan;

determining an amount of violation of the at least one constraint based on comparing the at least one constraint and the calculated organ dose;

calculating a reduction coverage volume for the planning target volume based on the determined amount of violation;

generating a virtual planning object by changing a volume of the organ at risk, such that an overlap region of the virtual planning object with the planning target volume corresponds to the reduction coverage volume; and reducing the initial coverage volume of the planning target volume based on removing at least a part of said overlap region from the planning target volume, thereby generating an optimized planning target volume to be irradiated during the irradiation treatment.

2. The method according to claim 1, further comprising:
converting the calculated reduction coverage volume into a radius for the virtual planning object; and
wherein the virtual planning object is generated based on changing the volume of the organ at risk using said radius.

3. The method according to claim 1, wherein changing the volume of the organ at risk comprises increasing or decreasing the volume of the organ at risk.

4. The method according to claim 1, further comprising:
providing a list comprising a plurality of pairs of entries, each pair of entries specifying a radius of an auxiliary virtual planning object and an amount of overlap of the corresponding auxiliary planning object with the planning target volume; and
converting the calculated reduction coverage volume into a radius for the virtual planning object based on at least one of the pairs of entries of the list.

5. The method according to claim 1, wherein the step of generating the virtual planning object comprises:
generating a plurality of auxiliary planning objects based on changing the volume of the organ at risk by a different radius for each of the plurality of auxiliary planning objects; and
determining an amount of overlap of each of the plurality of auxiliary planning objects with the planning target volume.

6. The method according to claim 1, further comprising:
receiving a tolerated coverage volume for the planning target volume, wherein the tolerated coverage volume is indicative of a minimum volume of the planning target volume receiving a prescribed dose during the irradiation treatment; and
wherein the reduction coverage volume for the planning target volume is determined based on the amount of violation of the at least one constraint and based on the tolerated coverage volume.

7. The method according to claim 1, further comprising:
calculating a dose distribution for at least a part of the planning target volume and at least a part of the organ at risk based on an optimization function; and wherein at least a part of the overlap region of the virtual planning object with the planning target volume is disregarded in the calculation of the dose distribution.

8. The method according to claim 1, wherein at least the steps of calculating an organ dose, determining an amount of violation, calculating a reduction coverage volume, and generating a virtual planning object are repeated in an iteration process.

9. The method according to claim 8, further comprising: calculating, in each iteration of the iteration process, an optimized organ dose deposited in at least a part of the organ at risk; and determining an optimized amount of violation of the at least one constraint of the organ at risk based on comparing the at least one constraint and the optimized dose deposited in said at least part of the organ at risk.

10. The method according to claim 1, further comprising: providing a voxel representation of at least a part of a patient, wherein the voxel representation comprises the planning target volume and the organ at risk, wherein the step of reducing the initial coverage volume comprises:

determining one or more voxels of the planning target volume arranged at least partly in the overlap region of the virtual planning object with the planning target volume; and removing at least a subset of the determined one or more voxels from the planning target volume to generate the optimized planning target volume.

11. The method according to claim 1, wherein the generation of the virtual planning object comprises isotropically changing the volume of the organ at risk in three spatial directions.

12. The method according to claim 1, wherein the generation of the virtual planning object comprises non-isotropically changing the volume of the organ at risk in three spatial directions.

13. A non-transitory computer medium comprising instructions, which, when running on at least one processor of at least one computer, causes the at least one processor to perform the steps of:

providing an initial coverage volume for a planning target volume to be irradiated in an irradiation treatment with a prescribed dose;

providing at least one constraint for an organ at risk, the at least one constraint being indicative of an allowed dose deposited in at least a part of the organ at risk;

calculating an organ dose deposited in said at least part of the organ at risk when applying an initial irradiation treatment plan;

determining an amount of violation of the at least one constraint based on comparing the at least one constraint and the calculated organ dose;

calculating a reduction coverage volume for the planning target volume based on the determined amount of violation;

generating a virtual planning object by changing a volume of the organ at risk, such that an overlap region of the virtual planning object with the planning target volume corresponds to the reduction coverage volume; and reducing the initial coverage volume of the planning target volume based on removing at least a part of said overlap region from the planning target volume, thereby generating an optimized planning target volume to be irradiated during the irradiation treatment.

14. A system comprising:
one or more processors and memory operably coupled with the one or more processors, wherein the memory stores instructions that, in response to execution of the instructions by the one or more processors, cause the one or more processors to perform the following operations:

providing an initial coverage volume for a planning target volume to be irradiated in an irradiation treatment with a prescribed dose;

providing at least one constraint for an organ at risk, the at least one constraint being indicative of an allowed dose deposited in at least a part of the organ at risk;

calculating an organ dose deposited in said at least part of the organ at risk when applying an initial irradiation treatment plan;

determining an amount of violation of the at least one constraint based on comparing the at least one constraint and the calculated organ dose;

calculating a reduction coverage volume for the planning target volume based on the determined amount of violation;

generating a virtual planning object by changing a volume of the organ at risk, such that an overlap region of the virtual planning object with the planning target volume corresponds to the reduction coverage volume; and reducing the initial coverage volume of the planning target volume based on removing at least a part of said overlap region from the planning target volume, thereby generating an optimized planning target volume to be irradiated during the irradiation treatment;

at least one electronic data storage device storing at least patient data; and a medical device,
wherein the one or more processors are operably coupled to the at least one electronic data storage device and the medical device;

wherein the at least one electronic data storage device is for acquiring, from the at least one data storage device, at least the patient data, and the medical device is for issuing a control signal to the medical device for controlling an operation of the medical device on a basis of the generated optimized planning target volume.

15. The system according to claim 14, wherein the medical device comprises:

a radiation treatment apparatus comprising a treatment beam source and a patient support unit, wherein the one or more processors are operably coupled to the radiation treatment apparatus for issuing a control signal to the radiation treatment apparatus for controlling, on the basis of the generated optimized planning target volume, at least one of an operation of the treatment beam source, and
a position of the patient support unit.

* * * * *

UNITED STATES PATENT AND TRADEMARK OFFICE
CERTIFICATE OF CORRECTION

| | | |
|---|---|---|
| PATENT NO. | : 11,273,328 B2 | Page 1 of 1 |
| APPLICATION NO. | : 16/328653 | |
| DATED | : March 15, 2022 | |
| INVENTOR(S) | : Stefan Schell et al. | |

It is certified that error appears in the above-identified patent and that said Letters Patent is hereby corrected as shown below:

In the Specification

In Column 2, Line 13, delete "Emplary" and insert -- Exemplary --, therefor.

In Column 9, Line 37, after "1" insert -- % --.

In Column 16, Line 42, after "apply" insert -- for --.

Signed and Sealed this
Sixth Day of September, 2022

Katherine Kelly Vidal
*Director of the United States Patent and Trademark Office*